(12) United States Patent
Choi et al.

(10) Patent No.: US 7,736,643 B2
(45) Date of Patent: Jun. 15, 2010

(54) METHOD FOR SCREENING OF A LIPASE HAVING IMPROVED ENZYMATIC ACTIVITY USING YEAST SURFACE DISPLAY VECTOR AND THE LIPASE

(75) Inventors: Eui-Sung Choi, Taejeon-si (KR); Jung-Hoon Sohn, Taejeon-si (KR); So-Young Kim, Gwacheon-si (KR)

(73) Assignee: Korea Research Institute of Bioscience and Biotechnology, Taejeon-si (KR)

( * ) Notice: Subject to any disclaimer, the term of this patent is extended or adjusted under 35 U.S.C. 154(b) by 488 days.

(21) Appl. No.: 10/527,438

(22) PCT Filed: Sep. 4, 2003

(86) PCT No.: PCT/KR03/01820

§ 371 (c)(1),
(2), (4) Date: Mar. 11, 2005

(87) PCT Pub. No.: WO2004/024954

PCT Pub. Date: Mar. 25, 2004

(65) Prior Publication Data

US 2006/0275760 A1 Dec. 7, 2006

(30) Foreign Application Priority Data

Sep. 13, 2002 (KR) .................. 10-2002-0055575

(51) Int. Cl.
 A61K 38/46 (2006.01)
 C12N 9/20 (2006.01)
 C12N 15/63 (2006.01)
 C12N 1/15 (2006.01)
 C07K 14/00 (2006.01)
 C07H 21/02 (2006.01)

(52) U.S. Cl. ................. 424/94.6; 435/198; 435/320.1; 435/254.11; 530/350; 536/23.1

(58) Field of Classification Search .............. None
See application file for complete search history.

(56) References Cited

U.S. PATENT DOCUMENTS 6,020,180 A * 2/2000 Svendsen et al. ............ 435/198

FOREIGN PATENT DOCUMENTS

WO WO 95/14783 6/1995
WO 02/12509 A1 2/2002

OTHER PUBLICATIONS

Kim et al. A cell surface display system using novel GPI-anchored proteins in Hansenula polymorpha. Yeast 19: 11153-1163. 2002.*
Kim et al. A cell surface display system using novel GPI-anchored proteins in Hansenula polymorpha. Yeast 19: 1153-1163. 2002. cover page.*
Patkar, S.A. et al. "Effect of mutation in non-consensus sequence Thr-X-Ser-X-Gly of *Candida antarctica* lipase B on lipase specificity, specific activity and thermostability", *Journal of Molecular Catalysis B: Enzymatic*, vol. 3 pp. 51-54, 1997.
Sawano, A. et al. "Directed evolution of green fluorescent protein by a new versatile PCR strategy for site-directed and semi-random mutagenesis", Nucleic Acids Research, vol. 28(16) pp. i-vii, 2000.
Uppenberg, J. et al. "The sequence, crystal structure determination and refinement of two crystal forms of lipase B from *Candida antarctica*", *Structure*, vol. 2(4) pp. 293-308, 1994.
Kim, Y.J. et al. "Effect of Linoleic Acid Concentration on Conjugated Linoleic Acid Production by *Butyrivibrio fibrisolvens* A38", *Applied and Environmental Microbiology*, vol. 66(12) pp. 5226-5230, 2000.
Kieke, M.C. et al. "Isolation of anti-T cell receptor scFv mutants by yeast surface display", *Protein Engineering*, vol. 10(11) pp. 1303-1310, 1997.
VanAntwerp, J.J. et al. "Fine Affinity Discrimination by Yeast Surface Display and Flow Cytometry", *Biotech. Prog.*, vol. 16 pp. 31-37, 2000.
Schreuder, M.P. et al. "Targeting of a Heterologous Protein to the Cell Wall of *Saccharomyces cerevisiae*", *Yeast*, vol. 9 pp. 399-409, 1993.
Murai, T. et al. "Development of an arming yeast strain for efficient utilization of starch by co-display of sequential amylolytic enzymes on the cell surface", *Appl Microbiol Biotechnol*, vol. 51 pp. 65-70, 1999.
Patkar, S. et al. "Effect of mutations in *Candida antarctica* B lipase", *Chemistry and Physics of Lipids*, vol. 93 pp. 95-101, 1998.
Shiraga, S. et al., "Construction of the combinatorial library of *Rhizopus oryzae lipase* mutated in the lid domain by displaying on yeast cell surface", *J. Molecular Catalysis B: Enzymatic*, vol. 17, issues 3-5, pp. 167-173, (Jun. 7, 2002).

* cited by examiner

*Primary Examiner*—Michele K Joike
(74) *Attorney, Agent, or Firm*—The Nath Law Group

(57) ABSTRACT

The present invention relates to a method for screening of the lipase having improved enzymatic activity using yeast surface display vector and the mutant lipase prepared by the same, more particularly to the method comprising; 1) cloning lipase gene into surface display vector, 2) preparing mutant lipase gene library of the step 1 by mutagenic PCR, 3) transforming the mutant lipase gene library of the step 2 and surface display vector into host cell, and 4) measuring the activity of the mutant lipase displayed in the surface of the transformed host cell and selecting the mutant lipase prepared by the same. The method of the present invention can screen the lipase having improved enzymatic activity. So, it can effectively be used for the various fields, such as food and detergent industry.

21 Claims, 7 Drawing Sheets

FIG. 2

```
                  *          20          *          40          *
LIP10.PRO  : MNIFYIPLFLLSFVQGTATPLVKRLPSGSDPAFSQPKSVLDAGLTCQGAS :  50
LIP14.PRO  : MNIFYIPLFLLSFVQGTATPLVKRLPSGSDPAFSQPKSVLDAGLTCQGAS :  50
WTLIP.PRO  : MNIFYIPLFLLSFVQGTATPLVKRLPSGSDPAFSQPKSVLDAGLTCQGAS :  50

*          60          *          80          *         100
LIP10.PRO  : PSSVSKPILLVPGTGTTGPQSFDSNWIPLSAQLGYTPCWISPPPFMLNDT : 100
LIP14.PRO  : PSSVSKPILLVPGTGTTGPQSFDSNWIPLSAQLGYTPCWISPPPFMLNDT : 100
WTLIP.PRO  : PSSVSKPILLVPGTGTTGPQSFDSNWIPLSAQLGYTPCWISPPPFMLNDT : 100

*         120          *         140          *
LIP10.PRO  : QVNTEYMVNAITTLYAGSGNNKLPVLTWSQGGLVAQWGLTPPPSIRSKVD : 150
LIP14.PRO  : QVNTEYMVNAITTLYAGSGNNKLPVLTWSQGGLVAQWGLTPPPSIRSKVD : 150
WTLIP.PRO  : QVNTEYMVNAITTLYAGSGNNKLPVLTWSQGGLVAQWGLTPPPSIRSKVD : 150

160          *         180          *         200
LIP10.PRO  : RLMAFAPDYKGTVLAGPLDALAVSAPSVWQQTTGSALTTALRNAGGLTQI : 200
LIP14.PRO  : RLMAFAPDYKGTVLAGPLDALAVSAPSVWQQTTGSALTTALRNAGGLTQI : 200
WTLIP.PRO  : RLMAFAPDYKGTVLAGPLDALAVSAPSVWQQTTGSALTTALRNAGGLTQI : 200

*         220          *         240          *
LIP10.PRO  : VPTTNLYSATDEIVQPQVSNSPLDSSYLFNGKNVQAQAVCGPIFVIDHAG : 250
LIP14.PRO  : VPTTNLYSATDEIVQPQVSNSPLDSSYLFNGKNVQAQAVCGPQFVIDHAG : 250
WTLIP.PRO  : VPTTNLYSATDEIVQPQVSNSPLDSSYLFNGKNVQAQAVCGPIFVIDHAG : 250

260          *         280          *         300
LIP10.PRO  : SLTSQPSYVVGRSALRSTTGQARSADYGITDCNPLPANDLTPEQKVAAAA : 300
LIP14.PRO  : SLTSQPSYVVGRSALRSTTGQARSADYGITDCNPLPANDLTPEQKVAAAA : 300
WTLIP.PRO  : SLTSQPSYVVGRSALRSTTGQARSADYGITDCNPLPANDLTPEQKVAAAA : 300

*         320          *         340
LIP10.PRO  : LPAPAAAAIVAGPKQNCEPDLMPYARPFAVGKRTCSGIVTPGS : 343  SEQ ID NO: 9
LIP14.PRO  : LPAPAAAAIVAGPKQNCEPDLMPYARPFAVGKRTCSGIVTPGS : 343  SEQ ID NO: 10
WTLIP.PRO  : LLAPAAAAIVAGPKQNCEPDLMPYARPFAVGKRTCSGIVTPGS : 343  SEQ ID NO: 19
```

FIG. 3
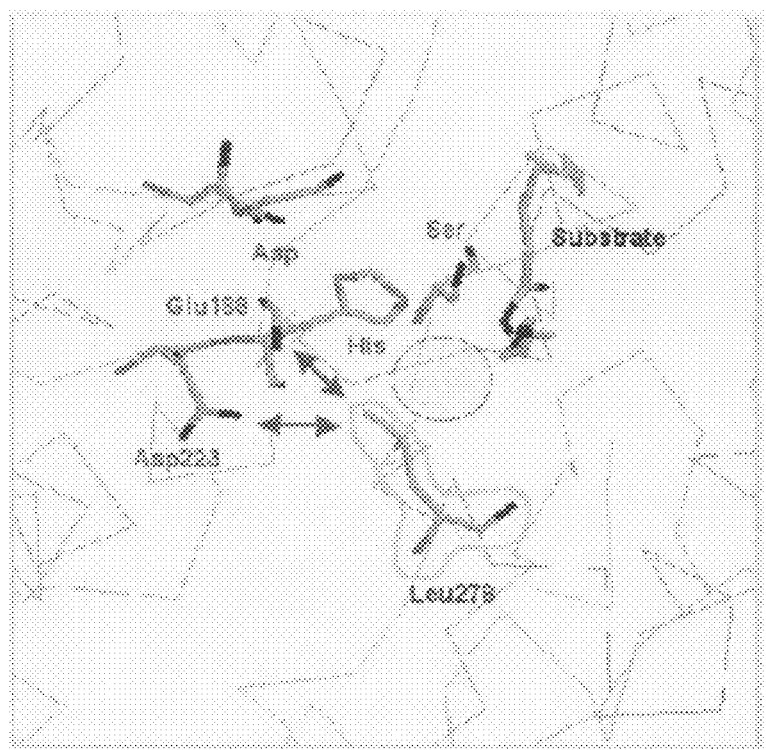
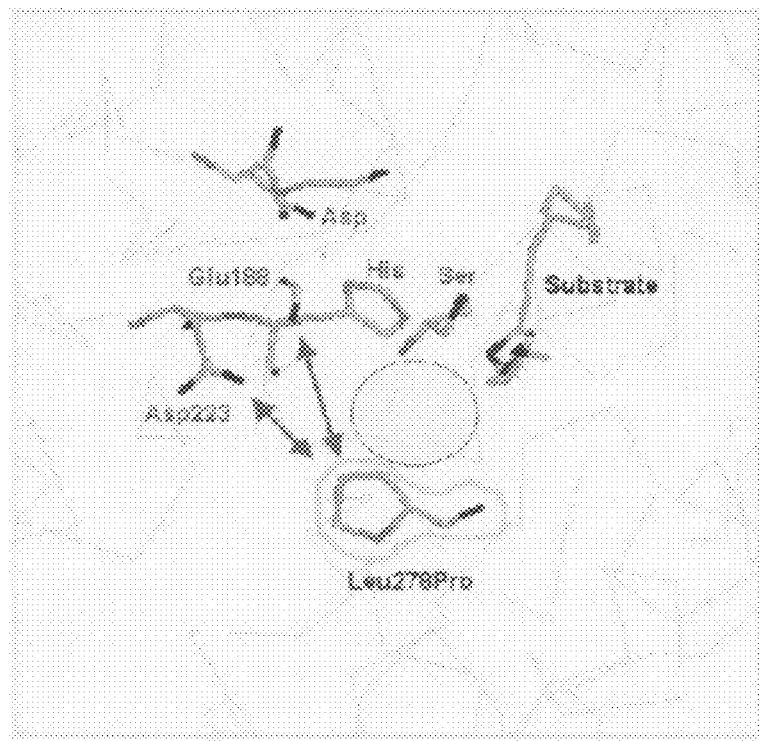

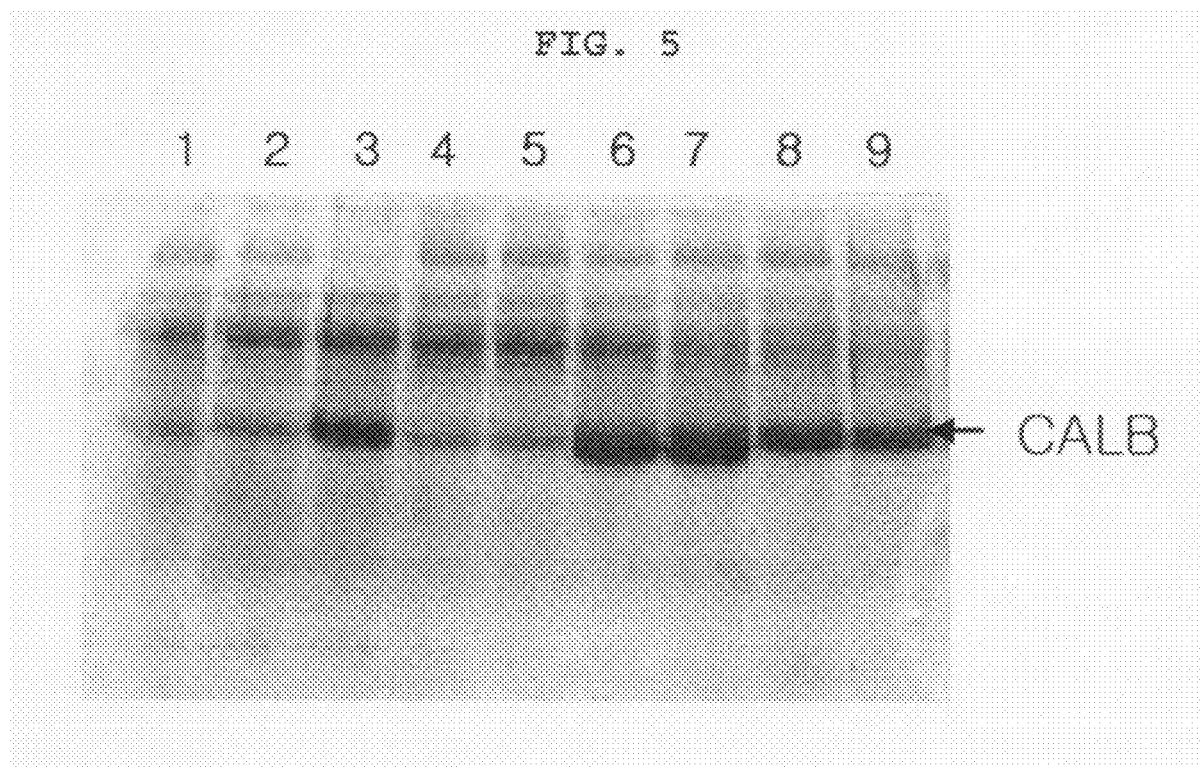

METHOD FOR SCREENING OF A LIPASE HAVING IMPROVED ENZYMATIC ACTIVITY USING YEAST SURFACE DISPLAY VECTOR AND THE LIPASE

FIELD OF THE INVENTION

The present invention relates to a method for screening of a lipase having an improved enzymatic activity using a yeast surface display vector and the mutant lipase prepared by the same, more particularly to the method comprising; 1) cloning lipase gene into a surface display vector, 2) preparing a mutant gene library of lipase of the step 1 by mutagenic PCR, 3) transforming the mutant lipase gene library of the step 2 and a surface display vector into a host cell, and 4) measuring the activity of the mutant lipase displayed in the surface of the transformed host cell and select the mutant lipase with evolved activity, and the mutant lipase prepared by the same.

BACKGROUND OF THE INVENTION

Lipase is a carboxylic ester hydrolase and is widely used for food and surfactant industry as well as the synthesis of various chiral compounds. Among many microorganism-originated lipases, *Candida antarctica*—originated lipase B (referred as 'CALB' hereinafter) is composed of 317 amino acids and gets into the form of α/β hydrolase.

CALB is industrially very important in the selection of optical isomers and in the synthesis of polyester (Anderson et al., *Biocatal. Biotransform.*, 1998, 16, 181), and can be used in variety of production of medical supplies and agricultural chemicals owing to the ability of optical conversion specifically with sec-alcohol and sec-amine (Rotticci et al., *Chembiochem.*, 2001, 2, 766).

Recently, studies to express foreign proteins on the cell surface of unicellular organism such as yeast, bacteria including bacteriophage, etc. have been actively undergoing and applied for the production of a new vaccine, the screening of antigens and antibodies, the fixation of useful enzymes onto cell surfaces, and so on. For example, researches on the expression of proteins on cell surface have been progressed using a kind of yeast (*Saccharomyces cerevisiae*). This yeast induces the secretion of a useful foreign protein in a medium without losing its activity by taking advantage of intracellular secretion system of higher eukaryotic cells, which makes the yeast a useful candidate as a host cell for the production of important foreign proteins by genetic recombination techniques. α-agglutinin, a widely known cell wall protein, has been a major target for the surface expression of yeast (Schreuder et al., *Yeast.*, 1993, 9, 399). Owing to α-agglutinin or other cell wall proteins, various enzymes such as α-galactosidase, glucoamylase, lipase, cutinase, etc. could be stably expressed on the cell surface.

In addition, according to a recent report, the development of industrially effective biocatalyst comes true by the simultaneous expression of various enzymes in a cell (Murai et al., *Appl. Microbiol. Biotechnol.*, 1999, 51, 65). As of today, microorganism-originated biocatalysts for the biological conversion for the production of food or medical supplies have been made by the steps of crushing cells, separating the expressed enzyme, and fixing the enzyme onto carrier or treating with penetrating solvent such as toluene. But, such process has a problem of low productivity because of high costs and inactivity of the enzyme.

Recently, studies on the screening method using *Saccharomyces cerevisiae*, which is adequate for the expression of target proteins on the cell surface have been undergoing. As an eukaryotic cell, yeast has a similar protein production process to higher animals, and has enough size for the cell selection by FACS (fluorescence activated cell sorter), which can differentiate cells with delicate differences (VanAntwerp and Wittrup., *Biotechnol. Prog.*, 2000, 16, 31). Using yeast expression system, manipulation of genes and a library construction can be simplified. Also, the difference of expression level can be overcome. It is also possible to select an enzyme which is most suitable for the surface expression, by screening with surface display system. The enzyme selected by this method can greatly enhance the use of the surface-expressed enzyme. While screening of yeast strains displaying antibodies, antigens or T-cell receptors with increased affinity using FACS has been reported a lot (Schreuder et al., *Vaccine.*, 1996, 14, 383, Kieke et al., *Protein. Eng.*, 1997, 10, 1303, Kieke et al., *Proc. Natl. Acad. Sci. USA.*, 1999, 96, 5651), the screening of strains displaying enzymes with increased activity has not yet been reported. Only the case that screening of carboxymethyl cellulase with increased activity by surface display system using ice nucleation protein originated from *Pseudomonas* sp has been reported so far (Kim et al., *Appl. Environ. Microbiol.*, 2000, 66, 788).

The present inventors isolated novel cell wall attachment-mediating proteins from the industrial yeast, *Hansenula polymorpha* and developed a novel surface display system expressing a target protein on a cell surface using the same (PCT/KR00/00819). The *Hansenula polymorpha* is an industrially effective strain which has strong inducible promoters, has a stability both in high temperature and organic solvents, grows fast and produces foreign recombinant proteins very well. So, the strain is very suitable for the biological reaction system and the production of enzyme like lipase.

In order to mass-produce lipase, a useful biological catalyst, the present inventors have constructed *Candida antarctica* lipase B mutant library using a surface expression system (PCT/KR00/00819) expressing a target protein on a cell surface, and have selected a mutant strain having an excellent lipase activity from the library, and finally have completed this invention by developing a novel method for mass-production of mutant lipase protein from the yeast strain.

DETAILED DESCRIPTION OF PREFERRED EMBODIMENTS

The present invention provides a method for screening of a mutant lipase having an improved enzymatic activity comprising the steps of 1) cloning a lipase gene into a surface display vector, 2) preparing a mutant lipase gene library by mutagenic PCR using the lipase gene in the expression vector of the step 1 as a template, 3) transforming the mutant lipase gene library of the step 2 and the surface display vector into host cells, and 4) measuring the activity of the mutant lipase displayed in the surface of the transformed host cell and selecting the lipase with improved activity from the mutant pool.

The present invention also provides a mutant lipase protein prepared by the screening method of the present invention, in which #219 leucine and/or #278 leucine of *Candida antarctica* lipase B represented by SEQ. ID. No 14 was replaced by other amino acids.

The present invention also provides a gene coding the mutant lipase protein.

The present invention also provides an expression vector containing the above gene.

The present invention also provides a transformant in which the above expression vector was introduced.

The present invention also provides a method for the production of the mutant lipase protein by cultivation of the above transformant.

Further features of the present invention will appear hereinafter.

The present invention relates to a method for screening of a mutant lipase having an improved enzymatic activity comprising the following steps:

1) Cloning a lipase gene into a surface display vector;
2) Preparing a mutant lipase gene library by mutagenic PCR using the lipase gene in the surface display vector of the step 1 as a template;
3) Transforming the mutant lipase gene of the step 2 and the surface display vector into host cells; and
4) Measuring the activity of the mutant lipase displayed in the surface of the transformed host cell selecting the lipase with improved activity from the mutant pool.

The 'surface display vector' in this invention means a vector expressing a foreign protein stably on a cell surface.

In this invention, *Candida antarctica* lipase B, represented by SEQ. ID. No 14 and originated from *Candida antarctica*, was preferably used for the cloning into the surface display vector.

The surface display vector used for the screening in this invention is the vector expressing a foreign protein on the surface of a transformant and is characterized by including a promoter gene, a gene coding a secretion signal sequence, a lipase gene or a mutant lipase gene, a surface display mediating gene and a terminator gene.

It is preferable to select a promoter gene from a group consisting of GAPDH, PGK, ADH, PHO5, GAL1, GAL10, SED1, MOX, TEF and TPI, select a gene coding a secretion signal sequence from a group consisting of Mf α, PHO6, SUC2, AMY, SED and killer toxin, and select a surface display mediating gene, a factor that can express lipase on the cell surface, from a group consisting of SED1, PIR2, TIP1, CWP1, GAS1 AND WSC1, but not always limited thereto.

As a host cell for the transfection in step 3 of the screening method in this invention, yeasts such as *Candida, Debaryomyces, Hansenula, Kluyveromyces, Pichia, Schizosaccharomyces, Yarrowia* and *Saccharomyces* genus, filamentous fungi such as *Aspergillus, Penicillium* and *Rhizopus* genus or bacteria such as *Escherichia* and *Bacillus* genus could be selected but it was not always limited thereto.

In the preferred embodiments of the present invention, the present inventors used the surface display vector that was introduced into the transformants (Accession Nos: KCTC 0824BP, KCTC 0825BP, KCTC 0826BP, KCTC 0827BP and KCTC 0828BP) that were deposited at Gene Bank of Korea Research Institute of Bioscience and Biotechnology (Korea Patent Application No: 2000-42939).

According to the screening method of the present invention, PCR was performed to induce mutation of a lipase gene after cloning the gene into the surface display vector. Host cells were transfected with the mutant gene. Then, the mutant gene was expressed in host cells. As a result, the mutant lipase was located on the surface of the transformant. Thus, the mutant lipase having high activity can be screened readily and fast by measuring the activity of the mutant lipase expressed on the surface of the transformant.

The present invention also provides a mutant lipase protein prepared by the screening method of the present invention, in which #219 leucine and/or #278 leucine of *Candida antarctica* lipase B represented by SEQ. ID. No 14 was replaced by other amino acids.

The present invention provides a mutant protein in which #219 amino acid and/or #278 amino acid of *Candida antarctica* lipase B (referred as "CALB" hereinafter) represented by SEQ. ID. No 14 was replaced by other amino acids.

The hydrophobic amino acid leucine of the mutant protein of the present invention that is #219 amino acid of CALB represented by SEQ. ID. No 14 is preferably replaced by a hydrophilic amino acid selected from a group consisting of glutamine, histidine, arginine, lysine, serine, threonine, asparagine and glutamic acid, and is more preferably substituted by glutamine, leading to be represented by SEQ. ID. No 11.

Also, #278 amino acid leucine of CALB represented by SEQ. ID. No 14 is preferably replaced by an amino acid selected from a group consisting of proline, tyrosine, phenylalanine, tryptophane and valine, and is more preferably substituted by a proline, making it be represented by SEQ. ID. No 9.

Also, #219 amino acid leucine of CALB represented by SEQ. ID. No 14 is preferably replaced by a hydrophilic amino acid selected from a group consisting of glutamine, histidine, arginine, lysine, serine, threonine, aspartic acid and glutamic acid and at the same time, #278 amino acid, leucine, is preferably replaced by an amino acid selected from a group consisting of proline, tyrosine, phenylalanine, tryptophane and valine. And #219 amino acid and #278 amino acid are more preferably substituted by glutamine or proline, respectively, in the same protein, making it be represented by SEQ. ID. No 10.

219 amino acid leucine of CALB is a hydrophobic amino acid exposed on the surface. When the above leucine is replaced by a hydrophilic amino acid, the stability in water increases, leading to the increase of the enzyme activity of a mutant protein. #278 amino acid leucine of CALB is located at $10^{th}$ α-helix of CALB that has been reported to work as a lid for lipase active site (Uppenberg et al., Structure., 1994, 2, 293). Many hydrophobic amino acids are included in $10^{th}$ α-helix region. Substitution of leucine therein with proline results in increasing the stability of helix structure, producing a bending structure (changing direction) and increasing the activity by changing the exposure level of active site. #278 amino acid leucine is located near #223 amino acid aspartic acid and #188 amino acid glutamic acid, giving the charge on the surface of active site. And if #278 amino acid is substituted with proline, the structure is changed, in which space taken by a hydrophobic leucine gets narrow and an active site is extended, making a more stable space for #223 and # 188 charged amino acids and making a more space for water molecules. The water molecule stabilizes a substrate on the active site and leads the increase of the activity.

The enzyme activity was measured with cell culture supernatants of a transformant producing a secreted form of mutant lipase protein. As a result, the affinities to substrates of the mutant proteins having amino acid sequences represented by SEQ. ID. No 9, No 10 and No 11 were similar each other, but had 5 times, 10 times and three times higher enzyme activity respectively than a wild type CALB (see Table 3).

The enzyme activity was also measured with whole cell fraction of the transformant expressing the mutant lipase protein of the present invention on the surface. As a result, the mutant proteins having amino acid sequences represented by SEQ. ID. No 9 and No 10 showed 5 times higher activity than a wild type CALB (see Table 1).

Thus, the mutant lipase protein of the present invention is confirmed to have higher enzyme activity than a wild type lipase protein.

The present invention also provides a gene coding the mutant lipase protein.

It is preferable that the gene of the present invention is coding a mutant protein in which #219 amino acid of CALB is replaced by a hydrophilic amino acid selected from a group consisting of glutamine, histidine, arginine, lysine, serine, threonine, aspartic acid and glutamic acid, and is more preferable that the gene is represented by SEQ. ID. No 8.

It is also preferable that the gene of the present invention is coding a mutant protein in which #278 amino acid of CALB is replaced by an amino acid selected from a group consisting of proline, tyrosine, phenylalanine, tryptophane and valine, and is more preferable that the gene is represented by SEQ. ID. No 6.

It is also preferable that the gene of the present invention is coding a mutant protein in which #219 amino acid of CALB is replaced by a hydrophilic amino acid selected from a group consisting of glutamine, histidine, arginine, lysine, serine, threonine, aspartic acid and glutamic acid, and #278 amino acid is substituted with an amino acid selected from a group consisting of proline, tyrosine, phenylalanine, tryptophane and valine. And it is more preferable that the gene is represented by SEQ. ID. No 7.

The present invention also provides an expression vector including the said gene.

The expression vector of the present invention includes a gene coding the mutant lipase protein of the invention, and is prepared to express the mutant lipase protein on the cell surface.

The vector expressing the mutant lipase protein of the present invention is characterized by having a promoter gene, a gene coding a secretion signal sequence, a mutant lipase gene, a surface display mediating gene and a terminator gene.

The promoter gene of the surface display vector is preferably selected from a group consisting of GAPDH, PGK, ADH, PHO5, GAL1, GAL10, SED1, MOX, TEF and TPI, and the gene coding a secretion signal sequence is preferably selected from a group consisting of MF-α, PHO5, SUC2, AMY, SED and killer toxin. The surface display-mediating gene is a factor to express lipase on the cell surface, and is preferably selected from a cell wall constituting gene group consisting of SED1, PIR2, TIP1, CWP1, GAS1, and WSC1. However, the choice is not always limited thereto.

In the preferred embodiments of the present invention, the present inventors constructed an expression vector having base sequences represented by SEQ. ID. No 6, No 7 or No 8 which are the genes coding the mutant protein of the present invention.

The present invention also provides a transformant prepared by introducing the said surface display vector into host cells.

Particularly, the transformant of the present invention was prepared by introducing the said expression vector including the mutant lipase gene into host cells. Host cells for the present invention can be selected from yeasts such as *Candida, Debaryomyces, Hansenula, Kluyveromyces, Pichia, Schizosaccharomyces, Yarrowia* and *Saccharomyces* genus, filamentous fungi such as *Aspergillus, Penicillium* and *Rhizopus* genus or bacteria such as *Escherichia* and *Bacillus* genus, but the choice is not limited thereto.

In the preferred embodiments of the present invention, yeast was used as a host cell. Particularly, *Hansenula polymorpha* DL1-L, *Hansenula polymorph* A16 or *Saccharomyces cerevisiae* Y2805 was used as a host cell to prepare the transformant. In the present invention, the transformants were produced by transforming *Hansenula polymorph* DL-1 with the expression vectors containing lipase gene each represented by SEQ. ID. No 6 and No 7, and the transformants were named "*Hansenula polymorph*/pLGK Lip10" and "*Hansenula polymorph*/pLGK Lip14", which were deposited at Gene Bank of Korea Research Institute of Bioscience and Biotechnology on Jul. 31, 2002 (Accession Nos: KCTC 10320BP and KCTC 10321BP).

The present invention also provides a method for producing a mutant lipase protein by culturing the said transformant.

The transformant of the present invention is preferably cultured at 2° C.-20° C. lower temperature than usual host cell culturing temperature to produce the protein.

Particularly, *Hansenula* is preferably cultured at 25° C.-35° C., and *Saccharomyces* is preferably cultured at 20° C.-28° C. In the preferred embodiments of the present invention, it was confirmed that *Hansenula polymorpha* DL1-L could produce the largest amount of lipase when it was cultured at 25° C. *Hansenula polymorpha* A16 produced lipase the largest amount of lipase when it was cultured at 25° C., so did *Saccharomyces serevisiae* Y2805 when it was cultured at 20° C. (see FIG. 6).

In addition, after mass-culturing the transformant of the present invention by fed-batch culture, it was confirmed that cell growth and the activity of lipase in cell culture solution were excellent (see FIG. 7a) and CALB protein was also produced by 800 mg/l (see FIG. 7b).

BRIEF DESCRIPTION OF THE DRAWINGS

The application of the preferred embodiments of the present invention is best understood with reference to the accompanying drawings, wherein.

pGPD: GAPDH promoter,
KT: Killer toxin secretion signal sequence,
tUK: Unknown terminator,
c: Terminal region of HARS36,
BD: Bent DNA domain of HARS36,
ARS: Self-replicable sequence of HARS36,
Rep: Telomeric repeated sequence of HARS36.

FIG. 2 is a sequence diagram showing the comparison of amino acid sequences of CALB mutants Lip10 and Lip14 with that of wild type (Lip wt).

FIG. 3 is a set of schematic diagrams showing the comparison of the active site structure of CALB mutant with that of wild type.

A: Active site structure of wild type lipase,
B: Active site structure of mutant lipase.

Figure 4:
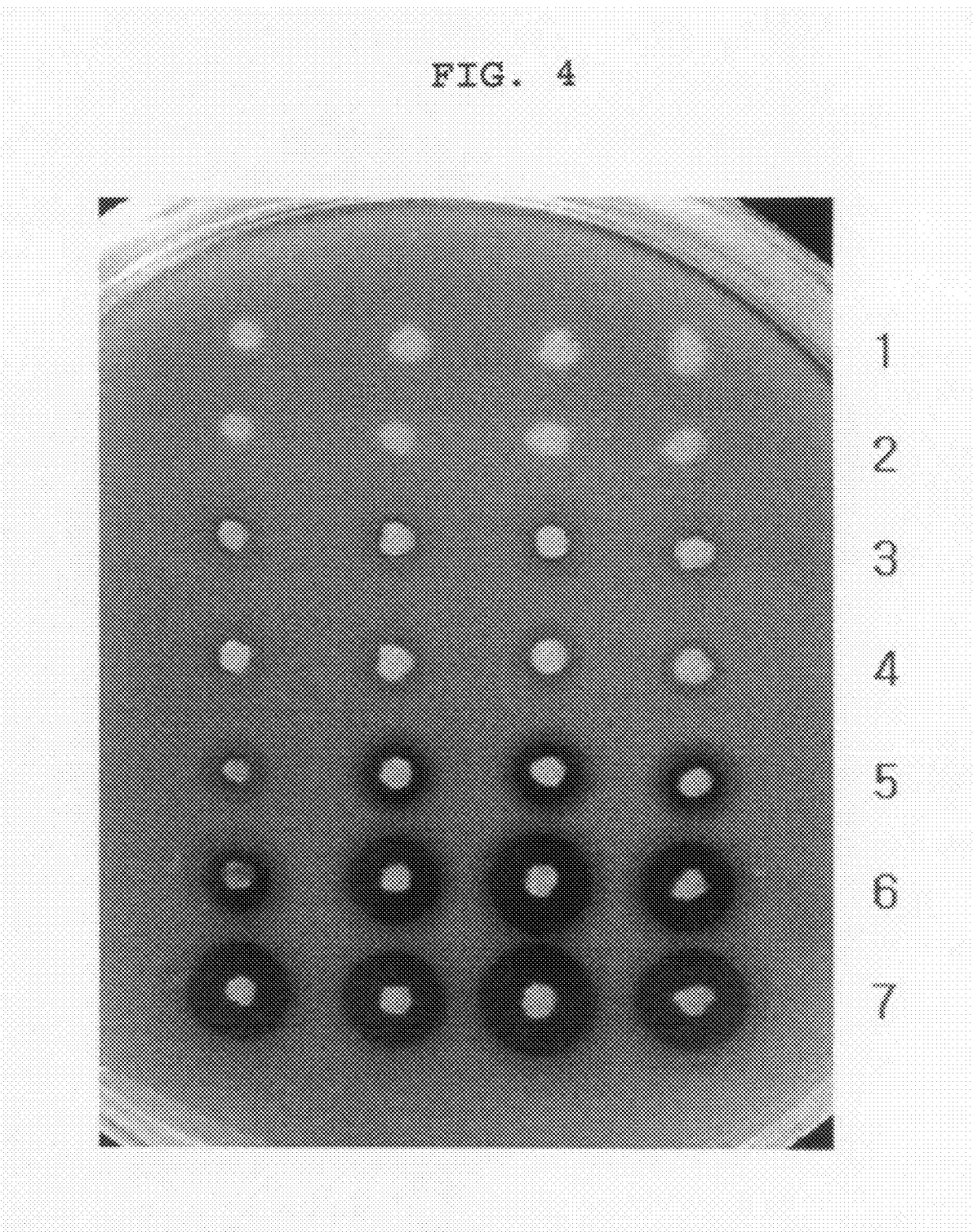

FIG. 4 is a photograph showing the activity of mutant CALB, which was confirmed on the plate medium.

Lane 1: Wt; wild type *Hansenula polymorpha* DL1 strain,
Lane 2: Lip-CwpF; a strain containing a vector displaying lipase on the surface (pLGK-Lip-CwpF),
Lane 3 and Lane 4: Lip10-CwpF and Lip14-CwpF; strains containing the surface display vector of Lip10 and Lip14,
Lane 5: Lip*; a strain containing a secretion vector of lipase (pLGK-Lip*),
Lane 6 and Lane 7: Lip10 and Lip14; strains containing the secretion vector of mutant lipase Lip10 and Lip14 (pLGK-Lip*).

FIG. 5 is a photograph showing the result of SDS-PAGE with the culture supernatants of CALB-displaying mutant strain.

Lane 1: Lipwt* strain,
Lane 2: Lip10* strain,
Lane 3: Lip14* strain,

Lane 4 and Lane 5: LP mutant strain,
Lane 6 and Lane 7: LQ mutant strain,
Lane 8 and Lane 9: LPQ mutant strain.

Figure 6A:
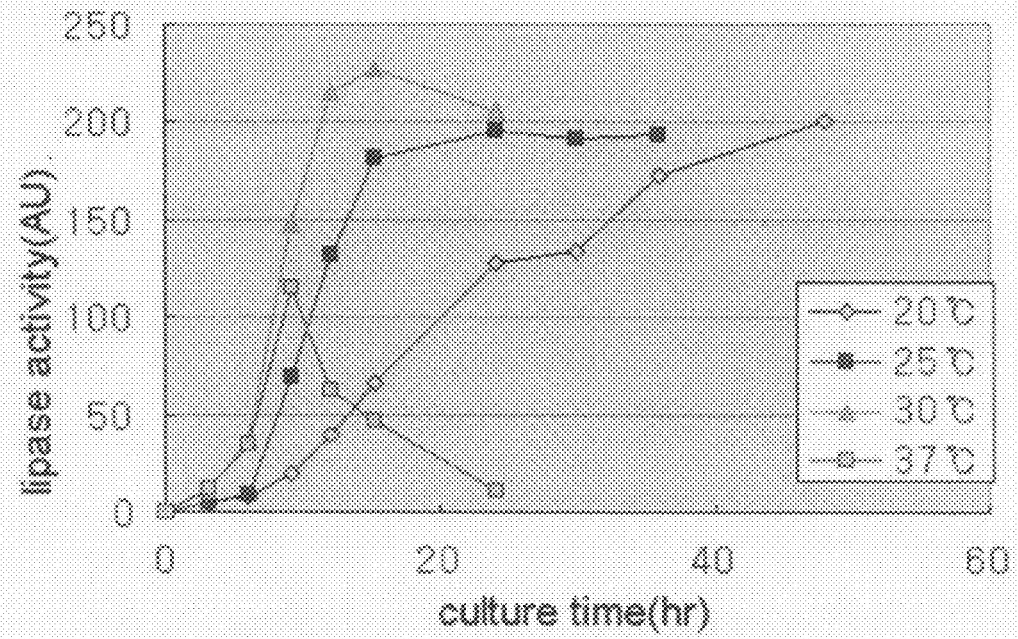

FIG. 6a is a graph showing the lipase activity of CALB, which was varied according to the culture temperature of *Hansenula polymorpha* DL1 strain.

Figure 6B:
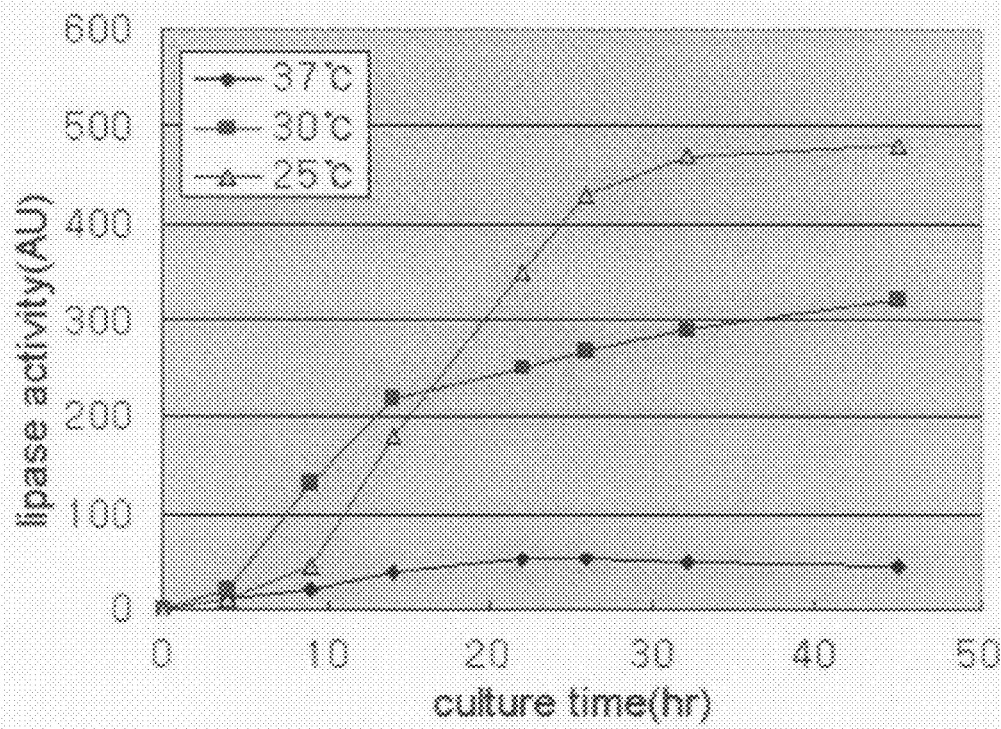

FIG. 6b is a graph showing the lipase activity of CALB, which was varied according to the culture temperature of *Hansenula polymorpha* A16 strain.

Figure 7A:
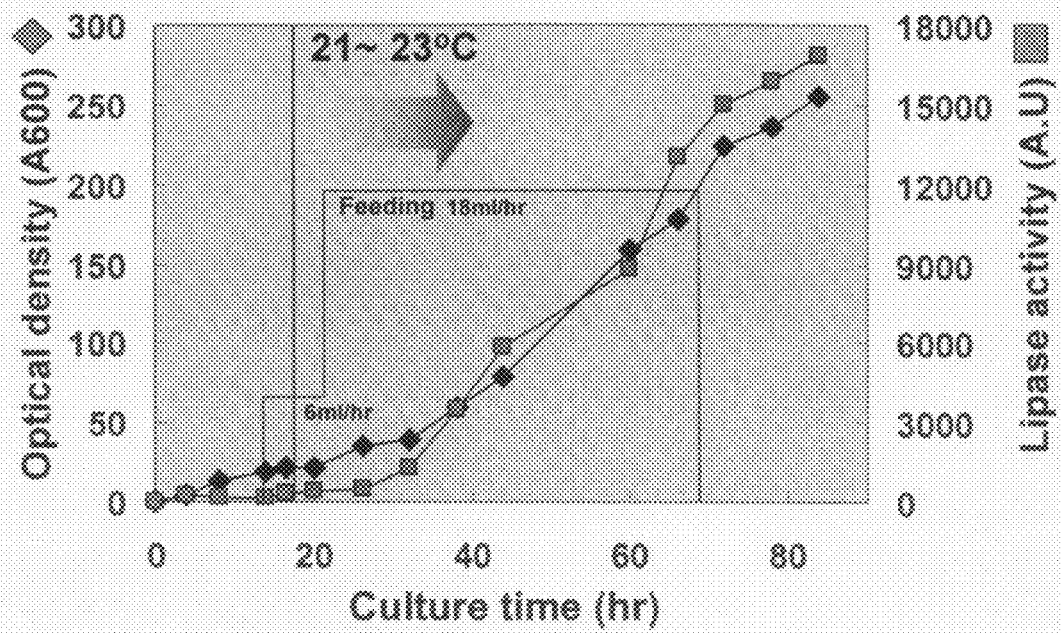

FIG. 7a is a set of graphs showing the cell growth (◇) measured at $OD_{600}$ with cell culture solution, after culturing *Saccharomyces cerevisiae* transformant, and the productivity of CALB (□) calculated by measuring the lipase activity in the culture solution.

Figure 7B:
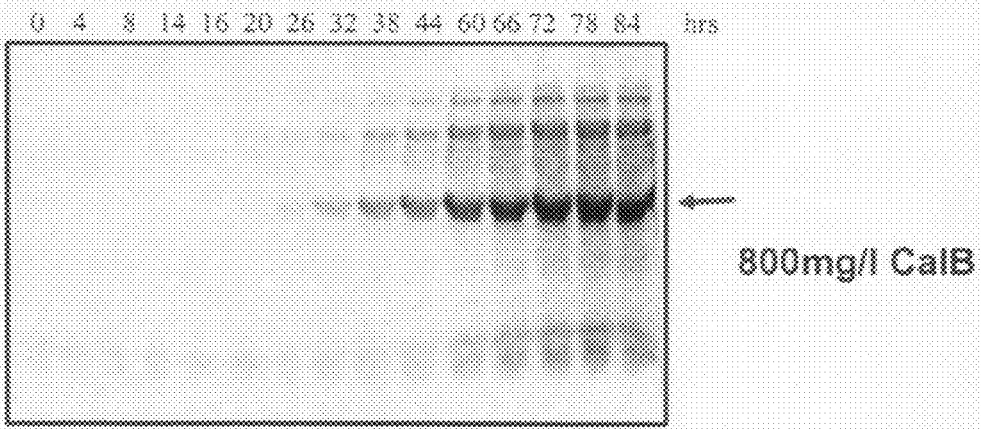

FIG. 7b is a photograph showing the amount of CALB protein produced in *Saccharomyces serevisiae* transformant culture, which was analyzed by SDS-PAGE.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of CALB Expressing Vector and Transformant

The present inventors constructed a vector expressing CALB on the surface of *H. polymorpha* or secreting the protein out of the cell.

Figure 1:
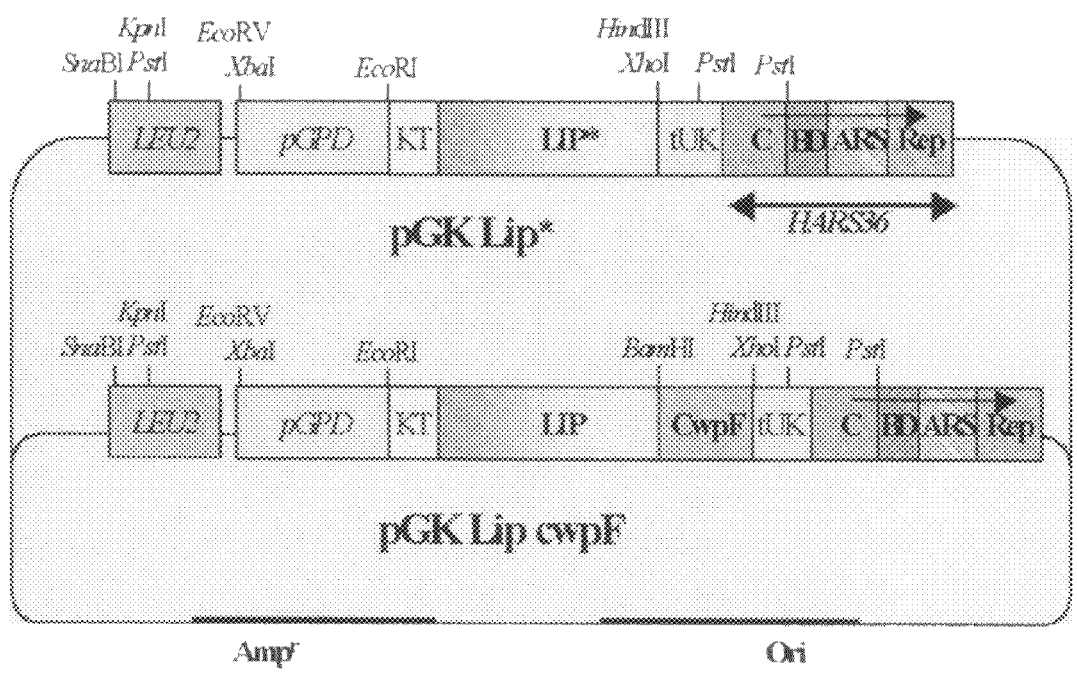
FIG. 1 is a schematic diagram showing the CALB secretion vector (pGK-Lip*) and the CALB surface display vector (pGK-Lip-CwpF).

Particularly, in order to construct a vector to secrete CALB to the media, CALB gene was first obtained from *Candida Antarctica* genome by polymerase chain reaction (PCR) using primers represented by SEQ. ID. No 1 and No 2. The PCR for the synthesis of CALB was performed using pfu polymerase (Stratagene, USA) at 94° C. for 3 minutes and 15 cycles of denaturation at 94° C. for 1 minute, annealing at 55° C. for 1 minute, and extension at 72° C. for 1 minute, followed by a final extension at 72° C. for 10 minutes. Thereafter, the gene was identified by sequencing analysis. CALB gene was digested with SapI to make it blunt-ended and digested again with BamHI. The gene was inserted into KpnI and BamHI regions of a vector, a kind of *Hansenula polymorpha* expression vector AMIpL1 (Agaphonov et al., *Yeast*, 1999, 15, 541) in which GAPDH promoter (Sohn et al., *Appl. Microbiol. Biotechnol.*, 1999, 51, 800) and killer toxin signal sequence (Sor and Fukuhara., *Curr. Genet.*, 1985, 9, 147) were inserted, by which the vector of the present invention was prepared, as seen in FIG. 1, and named "pGK-Lip*" (FIG. 1).

In order to prepare a vector expressing CALB on the cell surface, CALB gene was first obtained from *Candida Antarctica* genome by PCR using primers represented by SEQ. ID. No 1 and No 3, and the obtained gene was digested with the same method as the above, which was then inserted into AMIpL1 vector, resulting in the construction of pGK LipF vector. The surface display vector of the present invention was constructed by inserting CwpF (PCT/KR00/00819), a surface display mediator originated from CWP1 gene, into BamHI and Hind III region of pGK LipF, and then named "pGK-Lip-CwpF" (FIG. 2).

*Hansenula polymorpha* DL 1-L strain was transfected with the vector secreting CALB out of the cells (pGK-Lip*) and the other vector expressing CALB on the cell surface (pGK-Lip-CwpF) following Li/TE method (Hill et al., *Nucl. Acids. Res.*, 1991, 19, 5971), and then the transformants were selected from minimal medium (0.67% amino acid-defected yeast substrate and 2% glucose). The obtained transformant was transferred onto YPD plate medium (1% yeast extract, 2% peptone and 2% glucose) containing 1% tributyline and the activity of the transformant was detected by measuring the size of a ring around the strain.

As a result, the expression of CALB was confirmed by the presence of the active ring around the transformant.

Example 2

Construction of a Library by In Vivo Recombination

In order to establish CALB mutant library, the present inventors used in vivo recombination, which was once reported in *S. cerevisiae* (Abecassis et al., *Nucleic. Acids. Res.*, 2000, 28, E88). For the establishment of CALB library, this method was adapted to *Hansenula polymorpha*.

In vivo recombination is the method in which cells are transfected with a vector fragment and a synthesized insert fragment having homology with the vector in both ends of the DNA fragment together, so that an authentic circular vector is produced by the recombination therein. The in vivo recombination is simple and efficient method with no need to establish a library in advance in *E. coli*, so the method can be effectively used especially for the establishment of a library composed of genes fatal to *E. coli*.

The pGK-Lip-CwpF, a vector expressing CALB on the cell surface, was digested with EcoRI/PstI, resulting in the obtainment of 5 kb fragment. The fragment was recovered through gel and used as a vector fragment for the transformation. PCR was performed using PCR premix kit (Bioneer, Korea) with primers represented by SEQ. ID. No 4 and No 5 prepared by the cross of the vector fragment and 100 bp of HARS 36 region at 94° C. for 3 minutes and 25 cycles of denaturation at 94° C. for 30 seconds, annealing at 55° C. for 30 seconds, and extension at 72° C. for 1 minute, followed by a final extension at 72° C. for 7 minutes. At this time, pGK-Lip-CwpF was used as a substrate. At last, 100 ng of the resultant fragment was used for the transformation of *Hansenula polymorpha* strain along with 100 ng of vector fragment by using Li/TE method.

The transformed strains were randomly selected to measure the lipase activity on YPD flat medium containing 1% tributyline, leading to the confirmation of constructed library having a uniform activity.

Example 3

Construction of CALB Mutant Library

In order to construct CALB mutant Library, the present inventors used error-prone PCR and in vivo recombination.

Particularly, error-prone PCR was performed with primers represented by SEQ. ID. No 4 and No 5 using pGK-Lip-CwpF, a vector expressing CALB on the cell surface, as a template. PCR random error-prone kit (Clontec, USA) was used to induce 2-5 errors per 1 kb. DNA fragments were recovered after being cut by required size on gel. Amplification PCR was performed with those fragments by using PCR premix kit (Bioneer, Korea) with primers represented by SEQ. ID. No 4 and No 5 at 94° C. for 3 minutes and 25 cycles of denaturation at 94° C. for 30 seconds, annealing at 55° C. for 30 seconds, and extension at 72° C. for 1 minute, followed by a final extension at 72° C. for 7 minutes.

100 ng of the fragment obtained by the above process and 100 ng of the 5 kb vector fragment obtained by digesting pGK-Lip-CwpF with EcoRI/PstI were mixed and transfected into *Hansenula polymorpha* strain by using Li/TE method.

As a result, about $1 \times 10^4$ transformed strains were obtained.

Example 4

CALB Mutant Selection

The present inventors selected CALB mutant having high lipase activity from the CALB mutant library constructed in the above <Example 3>.

About 7,000 strains of the mutant library were inoculated on YPD plate medium containing 1% tributyline and cultured for 24 hours. Then, 23 strains showing large activity circle were primarily screened. The primarily selected strains were inoculated in YPD liquid medium and cultured at 37° C. for 16 hours, followed by centrifugation at 5,000 rpm for 5 minutes to separate cell fraction and culture supernatant. The cell fraction was suspended in 50 mM tris buffer solution (pH 7.5), which was washed and then suspended again with the same buffer solution by the same amount.

In order to measure the lipase activity, ρ-nitrophenyl palmitate (referred as 'pNPP' hereinafter) was used as a substrate. Reaction solution was prepared by mixing 10 μl of 10 mM pNPP, 40 μl of ethyl alcohol and 950 μl of 50 mM tris buffer (pH 7.5), to which 100 μl of cell suspension was added. After the reaction for 2 hours at 25° C., $OD_{450}$ was measured. The method to measure the lipase activity using pNPP as a substrate is to measure the extinction level of pNP group at 405 nm. The pNP group is isolated from pNPP (pNP group and palmitate were combined therein) by lipase. In this invention, 1 unit of lipase activity is defined to be the enzyme activity isolating 1 uM of pNP group per 1 minute.

As a result, strains Lip14, Lip10 and Lip23, which all had excellent activity in whole cell fraction, were finally selected.

Example 5

Analysis of CALB Mutants

The present inventors analyzed the mutant genes of the three mutant strains obtained in the above <Example 4>.

In order to recover the CALB mutant gene, the genome of the mutant strain was first purified, which was used as a template. PCR was performed using PCR premix kit (Bioneer, Korea) with primers represented by SEQ. ID. No 4 and No 5 at 94° C. for 3 minutes and 25 cycles of denaturation at 94° C. for 30 seconds, annealing at 55° C. for 30 seconds, and extension at 72° C. for 1 minute, followed by a final extension at 72° C. for 7 minutes. DNA fragments were recovered from gel and the DNA sequences were analyzed.

As a result, DNA sequences of Lip10 and Lip14 were each represented by SEQ. ID. No 6 and No 7, and their corresponding amino acid sequences were represented by SEQ. ID. No 9 and No 10 respectively. And it was confirmed that the $278^{th}$ leucine of Lip10 and Lip14 was replaced by proline, and additionally the $219^{th}$ leucine of Lip14 was substituted with glutamine (FIG. 2).

The $278^{th}$ leucine is located at the $10^{th}$ α-helix of CALB and the region has been reported as a lid structure of the lipase active site (Uppenberg et al., *Structure.*, 1994, 2, 293). Many hydrophobic amino acids are presented in the $10^{th}$ α-helix and leucine is one of them. As the amino acid is substituted with proline, helix structure becomes more stable and even a bending structure (change of directions) can be developed, leading to the increase of the activity by changing the exposure level of the active site. The $278^{th}$ leucine locates near the $188^{th}$ glutamic acid and the $223^{rd}$ aspartic acid having charge on the surface of the active site. When the amino acid is substituted with proline, the space for hydrophobic ends of $278^{th}$ leucine becomes narrower but the space for the $223^{rd}$ aspartic acid and the $188^{th}$ glutamic acid becomes larger, resulting in the change of the active site. In addition, the extended space can have water molecules that can contribute to the increase of the activity by making a substrate stay stable on the active site (FIG. 3). The $219^{th}$ leucine is a hydrophobic amino acid that is exposed on the surface and is replaced by a hydrophilic amino acid glutamine. CALB is an enzyme having mostly hydrophobic amino acids on its surface. The exposure of hydrophilic amino acids on the surface of a protein causes the change of a form and increases the stability in water. As for Lip23, the ends of CALB gene hold termination codon, by which secretory lipase was produced, suggesting the increase of lipase activity.

Example 6

Measurement of the Activity of CALB Mutant Strains

The present inventors measured the enzyme activity of lipase using CALB mutant strain selected in the above <Example 4>.

In order to construct a vector to express a gene on the cell surface, genomes of mutant strain and wild type CALB-expressing strain were isolated, which were used as templates for PCR. PCR was performed using PCR premix kit (Bioneer, Korea) with primers represented by SEQ. ID. No 4 and No 5 at 94° C. for 3 minutes and 25 cycles of denaturation at 94° C. for 30 seconds, annealing at 55° C. for 30 seconds, and extension at 72° C. for 1 minute, followed by a final extension at 72° C. for 7 minutes. The obtained DNA fragments were digested with EcoRI/ClaI and were inserted into a single copy integration vector 'AMIpLD1' (Agaphonov et al., *Yeast.*, 1999, 15, 541) along with GAPDH promoter to prepare a vector to express a gene on the cell surface. The produced vectors were named 'pLGK-Lip10-CwpF' and 'pLGK-Lip14-CwpF'.

In order to construct a vector to secrete a gene product to the media, genomes of mutant strain and wild type strain were isolated, which were used as templates for PCR. PCR was performed using PCR premix kit (Bioneer, Korea) with primers represented by SEQ. ID. No 1 and No 2 at 94° C. for 3 minutes and 25 cycles of denaturation at 94° C. for 30 seconds, annealing at 55° C. for 30 seconds, and extension at 72° C. for 1 minute, followed by a final extension at 72° C. for 7 minutes. The obtained DNA fragments were inserted into EcoRI/BamHI site of AMIpLD1 along with GAPDH promoter to construct vectors pLGK-Lip10* and pLGK-Lip14*.

After confirming the introduction of wild type and mutant CALB in the vector by the DNA sequencing, *Hansenula polymorpha* DL1-L strain was transformed by Li/TE method, and single copy integration to LEU2 site of the genome was confirmed by Southern blot analysis. The obtained transformant was inoculated on plate medium containing 1% tributyline, and cultured at 37° C. for 24 hours. The change of activity was investigated by observing the generated activity circle (FIG. 4). The transformant was cultured again in YPD liquid medium for 16 hours, followed by centrifugation to separate whole cell fraction and culture supernatant. The enzyme activity was measured using pNPP as a substrate.

As a result, 5 times increased lipase activity was observed in two kinds of mutant strains when they displayed on the cell surface. When the lipase was secreted out of cells, the activity in culture supernatant was confirmed to be increased 5 times (Lip10) and 10 times (Lip14) respectively, comparing to the wild type (Table 1).

TABLE 1

Comparison of wild type and mutant CALB lipase activity of *Hansenula polymorpha*

| Activity in culture supernatant(U/l) | |
|---|---|
| Lip* | 15,255 |
| Lip10* | 86,535 |
| Lip14* | 164,700 |
| Activity in whole cell fraction (U/l) | |
| Lip CwpF | 174 |
| Lip10 CwpF | 831 |
| Lip14 CwpF | 765 |

Also, the culture supernatant of strain secreting CALB was investigated by 12% SDS-PAGE and the results were confirmed by silver staining (FIG. 5). While the strain expressing Lip10 showed the equal quantity of CALB band to the strain expressing wild type CALB, the strain expressing Lip14 showed much more quantity of CALB band than other strains. The strain containing secretory form of Lip14 showed 2 times higher lipase activity than the strain containing Lip10, and it was mainly because the Lip14 was much effectively secreted into the media. As for the surface displayed lipase, the activities from the whole cell fraction were not varied between strains, suggesting that when a foreign protein is expressed on the cell surface, only a limited amount of protein is translocated onto the surface, making the secretion levels even.

Example 7

Purification of CALB from Mutant Strains and Analysis of the Characteristics Thereof The present inventors separated and purified wild type CALB and mutant CALB for the accurate analysis of the characteristics of the mutant CALB.

Each strain secreting CALB was cultured in YPD medium for 18 hours, followed by centrifugation at 5,000 rpm for 5 minutes to obtain culture supernatant. The culture supernatant was 10-fold concentrated by ultrafiltration. After then, ammonium sulfate was added into the protein solution until the concentration of ammonium sulfate was adjusted to 1 M. Let the recovered solution pass through butyl sepharose CL-4B column (Pharmacia, USA) saturated with 50 mM, pH 6.5 phosphate buffer containing 1 M ammonium sulfate. The concentration was lowered by 100% water to elute proteins. Among the eluted protein fractions, only the fractions showing lipase activity were recovered, which were concentrated again by ultrafiltration, and then, purified by using superdex-G200 gel filtration column chromatography (Pharmacia, USA). The purified Lip10, Lip14 and wild type lipase (Lip wt) were-obtained.

The mutant protein and the wild type protein were compared by measuring Km and Kcat with the purified proteins when pNPP was used as a substrate. 10 μl of protein solution was added to lipase reaction solution prepared by supplementing pNPP at serial different concentration. The optical density of the isolated pNP group was measured at 405 nm to determine Vi.

Km value of each protein was calculated by applying Michales-Menten equation using the Vi. As a result, Km values of both Lip10 and Lip14 were not increased. On the other hand, Kcat value of each protein was increased more than 6.5 times, suggesting that the activity of Lip10 and Lip14 was increased without changing the affinity to substrate (Table 2). The remaining activity of the protein was also measured after letting the protein at 50° C. for 10 minutes to test the heat stability. As a result, there was no big difference between the mutant protein and the wild type protein in heat stability. Stereoselectivity was also measured by using (R,S)-acetyl ester as a substrate. As a result, there was no big difference between the mutant protein and the wild type protein in stereoselectivity.

So, each mutant protein was confirmed to have 6-fold increased enzyme activity without damaging the stability and specificity of the protein.

TABLE 2

CALB activity of each mutant strain

| | Km(μmol) | Vmax | Kcat(S-1p mol-1) |
|---|---|---|---|
| Lip wt | 20.4 | 1.99 | 130.9 |
| Lip10 | 21.4 | 12.9 | 850.9 |
| Lip14 | 23.8 | 13.7 | 898.0 |

Example 8

Analysis of the Mutation Characteristics Using Site-Directed Mutagenesis

The present inventors investigated the mutation characteristics by using site-directed mutagenesis to confirm whether the characteristic change of mutant protein was solely caused by the change of amino acid.

L278P (the $278^{th}$ leucine was replaced by proline, which was present both in Lip10 and Lip14) mutation and L219Q (the $219^{th}$ leucine was replaced by glutamine, which was present only in Lip14) mutation were induced by PCR for the site-directed mutagenesis in wild type gene, and analyzed their effect. For the site-directed mutagenesis, PCR was performed using pfu polymerase and wild type CALB gene as a substrate with primers represented by SEQ. ID. No 15, No 16, No 17 and No 18 at 94° C. for 3 minutes and 15 cycles of denaturation at 94° C. for 1 minute, annealing at 55° C. for 1 minute, and extension at 72° C. for 1 minute, followed by a final extension at 72° C. for 10 minutes.

In order to synthesize L278P mutant gene, one gene was prepared by PCR with primers represented by SEQ. ID. No 2 and No 17 using wild type gene as a substrate. The other gene was also synthesized by PCR with primers represented by SEQ. ID. No 4 and No 18. The two synthesized DNA fragments were mixed, and the mixture was used as a substrate for PCR with primers represented by SEQ. ID. No 2 and No 4, resulting in the connection of the two gene fragments. At that time, 5 μl of each gene fragment and 3 μl of each primer were added into the PCR reaction mixture, and then PCR was performed using ExTaq polymerase (Dakara, Japan) at 94° C. for 3 minutes and 20 cycles of denaturation at 94° C. for 30 seconds, annealing at 55° C. for 30 seconds, and extension at 72° C. for 90 seconds, followed by a final extension at 72° C. for 7 minutes. The gene synthesized by the above method was digested with EcoRI/ClaI, which was inserted into the corresponding region of the vector 'pLGK-Lip-CwpF' and then named 'pLGK-LP'.

In order to synthesize L219Q mutant gene represented by SEQ. ID. No 8, one gene was prepared by PCR with primers represented by SEQ. ID. No 2 and No 15 using wild type gene as a substrate. The other gene was also synthesized by PCR with primers represented by SEQ. ID. No 4 and No 16. The two synthesized DNA fragments were mixed, and the mixture was used as a substrate for PCR with primers represented by SEQ. ID. No 2 and No 4, resulting in the connection of the two gene fragments. At that time, 5 µl of each gene fragment and 3 µl of each primer were added-into the PCR reaction mixture, and then PCR was performed using ExTaq polymerase (Dakara, Japan) at 94° C. for 3 minutes and 20 cycles of denaturation at 94° C. for 30 seconds, annealing at 55° C. for 30 seconds, and extension at 72° C. for 90 seconds, followed by a final extension at 72° C. for 7 minutes. The gene synthesized by the above method was digested with EcoRI/ClaI, which was inserted into the corresponding region of the vector 'pLGK-Lip-CwpF' and then named 'pLGK-LQ'.

In order to obtain a gene inducing both L278P mutation and L219Q mutation, PCR was performed with primers represented by SEQ. ID. No 2, No 15, No 4 and No 16 using pLGK-LP gene as a substrate, resulting in the construction of 'pLGK-LPQ' following the same process as the above. Hansenula polymorpha strain was transformed with each vector by Li/TE method. The transformants were cultured in YPD medium for 18 hours. After then, culture supernatant was recovered to measure the lipase activity by the same method as used above.

As a result, LP and LPQ showed similar increased activity as Lip10 and Lip14 (Table 3). LQ that was composed of amino acids represented by SEQ. ID. No 11 showed three times higher lipase activity than the wild type gene. Culture supernatant of each strain was compared by SDS-PAGE to investigate the cause of the increased LQ activity. As a result, LQ produced as many proteins as LPQ (FIG. 5).

TABLE 3

Comparison of activity of site-directed mutagenesis-induced CALB

| Lipase | Activity in culture supernatant (U/l) |
|---|---|
| Lip wt | 17,458 |
| Lip10 | 118,401 |
| Lip14 | 190,854 |
| LP | 98,890 |
| LQ | 48,850 |
| LPQ | 200,300 |

Thus, it was confirmed that L219Q mutation increased the protein productivity, while L278P mutation decreased the protein activity. Considering Kcat value, Lip14, rather than Lip10, was believed to have the effect of increasing the protein production and it's activity as well, suggesting that L219Q mutation was involved in variety of fields.

Example 9

Variation of CALB Expression According to the Culture Temperature

The present inventors measured CALB activity at various culture temperatures in order to determine the optimum culture condition for CALB.

The activity of Hansenula polymorpha DL1-L strain including pLGK-Lip14* was measured at different culture temperatures. The strain was inoculated in YPD medium, making the primary $OD_{600}$ 1 and cultured at 20° C., 25° C., 30° C. or 37° C., during which culture supernatants were recovered to measure the activity. To measure the activity, pNPP was used as a substrate and 10 µl of properly diluted cell culture supernatant was added into 200 µl of reaction mixture prepared by mixing 25 µl of 50 mM pNPP, 450 µl of ethyl alcohol and 9500 µl of 50 mM tris buffer (pH 7.5), which was reacted at 25° C. At last, Vi was measured at 405 nm. 1 AU (arbitrary unit) of lipase activity was defined to be the Vi value obtained under the above condition.

As a result, the culture supernatant from the cells grown at 25° C. showed the highest activity of lipase and growth. In the meantime, cultivation at 37° C. rather caused rapid decrease of the activity by the lapse of time (FIG. 6a).

That seemed to be the effect of protease secreted in cells during apoptosis. The experiment was repeated with Hansenula polymorpha A16 strain (CBS4732 derivative) that was known to be less affected by protease. Hansenula polymorpha A16 strain was transformed with pLGK-Lip14* by the same procedure as the above. The obtained transformant was inoculated in YPD medium, making the primary $OD_{600}$ 1, and then cultured at 25° C., 30° C. and 37° C. The culture supernatant was recovered to measure the activity.

As a result, it was confirmed that Hansenula polymorpha A16 strain, showed almost no change in the lipase activity with the Hansenula polymorpha DL-1 strain but expressed much more lipase as being cultured at low temperature (FIG. 6b). Cultivation at 25° C. for 30 hours led to the highest activity of lipase, producing 480 AU of the enzyme.

Example 10

CALB Expression in Saccharomyces cerevisiae

For the optimum production of enzyme, the mutant CALB was expressed in Saccharomyces cerevisiae.

Lip14 gene was synthesized by PCR using primers represented by SEQ. ID. No 2 and No 12, which was then linked to EcoRI/BamHI site of the vector 'YEGα HIR525' (Choi et al., Appl. Microbial. biotechnol., 1994, 42, 587) by the fusion with NdeI and α-amylase secretion signal sequence represented by SEQ. ID. No 13. Saccharomyces cerevisiae Y2805 (MATα pep4::HIS3 prb-1.6R can1 his3-20 ura3-52) strain was transformed with the obtained vector using Li/TE method. The transformants were selected using SC-URA (0.67% yeast substrate lacking in amino acids, 2% glucose and various other amino acids except uracil) medium. The selected transformants were cultured on YPDG (1% yeast extract, 2% peptone, 0.5% glucose and 1.5% galactose) medium containing 1% tributyline to measure the lipase activity.

As a result, the activity circle was observed on the plate. The confirmed strain was inoculated in YPDG liquid medium and induced to be expressed at 30° C. for 24 hours and the activity was measured.

In order to investigate if Saccharomyces cerevisiae was equally affected by the temperature during the culture, Saccharomyces cerevisiae was cultured at 20° C. and 30° C., respectively And culture supernatants were recovered to measure the activity.

As a result, when it was expressed at 20° C. (720 AU), the activity was 10 times as high as that when expressed at 30° C.

Example 11

Optimization for the Mass-Production of Improved CALB Using Fermentor

In order to mass-produce improved CALB using *Saccharomyces cerevisiae*, 5 μl fermentor was used for fed-batch culture to optimize CALB production. YPD medium (1% yeast extract, 4% peptone and 2% glucose) was used as the primary culture medium. YG medium (20% yeast extract and 40% galactose) was additionally supplied at intervals of 6-18 ml/hour to induce the expression of CALB protein. As stated above, the recombinant CALB producing strain (KCTC 10321BP) showed the best productivity at rather low temperature than the optimal culture temperature. Thus, culture temperature was set at 30° C. at early stage of culture to let the cell enter the log phase. Thereafter, culture temperature was lowered to 20-23° C. to make protein production best. At that time, galactose, an inducer, was added to the medium. After culture, cell growth was investigated by measuring $OD_{600}$ with cell culture medium, followed by measuring the lipase activity. The CALB protein produced by fed-batch culture was quantified by performing SDS-PAGE using the culture medium.

As a result, as shown in FIG. 7a, cell growth was observed until the $OD_{600}$ reached 300 and the maximum production of the improved CALB was 18,000 AU. Culture supernatants were recovered every hour and analyzed by SDS-PAGE. The result was shown in FIG. 7b. The production of improved CALB was 800 mg per liter.

INDUSTRIAL APPLICABILITY

As explained hereinbefore, the screening method for the mutant lipase of the present invention facilitates the preparation of a transformant producing mutant lipase having an improved enzymatic activity. The mutant lipase prepared from the said transformant can be fixed on cell surface and is reproductive, so that the mass-production is possible. Thus, the method of the present invention that can screen the lipase having an improved enzymatic activity can be effectively used for the various fields, such as food and detergent industry.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A mutant lipase protein of *Candida antarctica* lipase B comprising SEQ. ID. No 14, wherein the #219 leucine is replaced by a hydrophilic amino acid selected from a group consisting of glutamine, histidine, arginine, lysine, serine, threonine, aspartic acid and glutamic acid.

2. The mutant lipase protein as set forth in claim 1, wherein the #219 leucine is replaced by glutamine, and its amino acid sequence comprises SEQ. ID. No 11.

3. A polynucleotide encoding the mutant lipase protein of claim 1.

4. The polynucleotide as set forth in claim 3, wherein the #219 leucine is replaced by serine, in the mutant lipase protein, and the nucleotide sequence comprises SEQ. ID. No 8.

5. An expression vector comprising the polynucleotide of claim 3.

6. The expression vector as set forth in claim 5, wherein the vector comprises a promoter gene, a secretion signal sequence gene, a polynucleotide, wherein the #219 leucine is replaced by serine in the mutant lipase protein, and its nucleotide sequence comprises SEQ. ID. No. 8, a terminator gene and/or a surface display-mediating gene.

7. A transformant in which the expression vector of claim 5 is introduced.

8. A method for producing the mutant lipase protein of claim 1, comprising cultivating a transformant in which an expression vector comprising a polynucleotide encoding a mutant lipase protein is introduced, said mutant lipase protein comprising SEQ ID. No. 14 where the #219 leucine is replaced by a hydrophilic amino acid selected from a group consisting of glutamine, histidine, arginine, lysine, serine, threonine, aspartic acid and glutamic acid.

9. A mutant lipase protein of *Candida antarctica* lipase B comprising SEQ. ID. No 14, wherein the #278 leucine is replaced by proline, and its amino acid sequence comprises SEQ. ID. No 9.

10. A polynucleotide encoding the mutant lipase protein of claim 9.

11. An expression vector comprising the polynucleotide of claim 10.

12. A transformant in which the expression vector of claim 11 is introduced.

13. A method for producing the mutant lipase protein of claim 9, comprising cultivating a transformant in which an expression vector comprising a polynucleotide encoding a mutant lipase protein comprising SEQ ID. No. 9 is introduced.

14. A mutant lipase protein of *Candida antarctica* lipase B comprising SEQ. ID. No 14, wherein the #219 leucine is replaced by glutamine, and the #278 leucine is replaced by proline, and its amino acid sequence comprises SEQ. ID. No 10.

15. A polynucleotide, comprising a base sequence comprising SEQ. ID. No 7 coding the mutant lipase protein of claim 14.

16. An expression vector comprising the polynucleotide of claim 15.

17. A transformant in which the expression vector of claim 16 is introduced.

18. A method for producing the mutant lipase protein of claim 14 comprising cultivating a transformant in which an expression vector comprising a polynucleotide encoding a mutant lipase protein comprising SEQ ID. No. 10 is introduced.

19. The method as set forth in any of claims 8-18, wherein the culture temperature is 2° C.-20° C. lower than temperature of host cell culture.

20. The method as set forth in any of claims 8-18, wherein the culture temperature is 25° C.-35° C. and the transformant is *Hansenula*.

21. The method as set forth in any of claims 8-18, wherein the culture temperature is 20° C.-28° C. and the transformant is *Saccharomyces*.

* * * * *

UNITED STATES PATENT AND TRADEMARK OFFICE
CERTIFICATE OF CORRECTION

PATENT NO. : 7,736,643 B2
APPLICATION NO. : 10/527438
DATED : June 15, 2010
INVENTOR(S) : Eui-Sung Choi et al.

It is certified that error appears in the above-identified patent and that said Letters Patent is hereby corrected as shown below:

Column 32, Claim 19, Line 48
Please delete "2° C.-20° C. lower"
and replace with -- 2° C-20° C lower --

Column 32, Claim 20, Line 51
Please delete "25° C.-35° C. and"
and replace with -- 25° C-35° C and --

Column 32, Claim 21, Line 54
Please delete "20° C.-28° C. and"
and replace with -- 20° C-28° C and --

Signed and Sealed this

Thirty-first Day of August, 2010

David J. Kappos
*Director of the United States Patent and Trademark Office*

SEQUENCE LISTING

<160> NUMBER OF SEQ ID NOS: 19

<210> SEQ ID NO 1
<211> LENGTH: 27
<212> TYPE: DNA
<213> ORGANISM: Artificial Sequence
<220> FEATURE:
<223> OTHER INFORMATION: CALB primer 1

<400> SEQUENCE: 1
ggctcttcag ccactccttt ggtgaag                               27

<210> SEQ ID NO 2
<211> LENGTH: 23
<212> TYPE: DNA
<213> ORGANISM: Artificial Sequence
<220> FEATURE:
<223> OTHER INFORMATION: CALB primer 2

<400> SEQUENCE: 2
gcggatcctc aggggtgac gat                                    23

<210> SEQ ID NO 3
<211> LENGTH: 27
<212> TYPE: DNA
<213> ORGANISM: Artificial Sequence
<220> FEATURE:
<223> OTHER INFORMATION: CALB primer 3

<400> SEQUENCE: 3
gcggatccgg gggtgacgat gccggag                               27

<210> SEQ ID NO 4
<211> LENGTH: 19
<212> TYPE: DNA

```
<213> ORGANISM: Artificial Sequence
<220> FEATURE:
<223> OTHER INFORMATION: GPD-err primer

<400> SEQUENCE: 4
gcagagctaa ccaataagg                                                19

<210> SEQ ID NO 5
<211> LENGTH: 19
<212> TYPE: DNA
<213> ORGANISM: Artificial Sequence
<220> FEATURE:
<223> OTHER INFORMATION: T-0 primer

<400> SEQUENCE: 5
tgcagttgaa cacaaccac                                                19

<210> SEQ ID NO 6
<211> LENGTH: 1023
<212> TYPE: DNA
<213> ORGANISM: Candida antarctica

<400> SEQUENCE: 6
atgaatatat tttacatatt tttgtttttg ctgtcattcg ttcaaggtac cgccactccc    60
ttggtgaagc gtctgccttc cggttcggac cctgcctttt cgcagcccaa gtcggtgctc   120
gatgcgggtc tgacctgcca gggtgcttcg ccatcctcgg tctccaaacc catccttctc   180
gtccccggaa ccggcaccac aggtccacag tcgttcgact cgaactggat ccccctctct   240
gcgcagctgg gttacacacc ctgctggatc tcaccccgc cgttcatgct caacgacacc    300
caggtcaaca cggagtacat ggtcaacgcc atcaccacgc tctacgctgg ttcgggcaac   360
aacaagcttc ccgtgctcac ctggtcccag ggtggtctgg ttgcacagtg gggtctgacc   420
ttcttcccca gtatcaggtc caaggtcgat cgacttatgg cctttgcgcc cgactacaag   480
ggcaccgtcc tcgccggccc tctcgatgca ctcgcggtta gtgcaccctc cgtatggcag   540
caaaccaccg ttcggcact cactaccgca ctccgaaacg caggtggtct gacccagatc    600
gtgcccacca ccaacctcta ctcggcgacc gacgagatcg ttcagcctca ggtgtccaac   660
tcgccactcg actcatccta cctcttcaac gggaagaacg tccaggcaca ggctgtgtgt   720
gggccgctgt tcgtcatcga ccatgcaggc tcgctcacct cgcagttctc ctacgtcgtc   780
ggtcgatccg ccctgcgctc caccacgggc caggctcgta gtgcagacta tggcattacc   840
gactgcaacc ctcttcccgc caatgatctg actcccgagc aaaaggtcgc cgcggctgcg   900
ctcccggcgc cggcggctgc agccatcgtg gcgggtccaa gcagaactg cgagcccgac    960 ctcatgccct acgcccgccc ctttgcagta ggcaaaagga cctgctccgg catcgtcacc  1020
ccc                                                               1023

<210> SEQ ID NO 7
<211> LENGTH: 951
<212> TYPE: DNA
<213> ORGANISM: Candida antarctica

<400> SEQUENCE: 7
ctgccttccg gttcggaccc tgccttttcg cagcccaagt cggtgctcga tgcgggtctg    60
acctgccaag gtgcttcgcc atcctcggtc tccaaaccca tccttctcgt ccccggaacc   120
ggcaccacag gtccacagtc gttcgactcg aactggatcc cctctctgc gcagctgggt    180 tacacaccct gctggatctc accccgccg ttcatgctca acgacaccca ggtcaacacg    240
```

```
gagtacatgg tcaacgccat caccacgctc tacgctggtt cgggcaacaa caagcttccc    300
gtgctcacct ggtcccaggg tggtctggtt gcacagtggg gtctgacctt cttccccagt    360
atcaggtcca aggtcgatcg acttatggcc tttgcgcccg actacaaggg caccgtcctc    420
gccggccctc tcgatgcact cgcggttagt gcaccctccg tatggcagca aaccaccggt    480
tcggcactca ctaccgcact ccgaaacgca ggtggtctga cccagatcgt gcccaccacc    540
aacctctact cggcgaccga cgagatcgtt cagcctcagg tgtccaactc gccactcgac    600
tcatcctacc ttttcaacgg aaagaacgtc caggcacagg ctgtgtgtgg gccgcagttc    660
gtcatcgacc atgcaggctc gctcacctcg cagttctcct acgtcgtcgg tcgatccgcc    720
ctgcgctcca ccacgggcca ggctcgtagt gcggactatg gcattacgga ctgcaaccct    780
cttcccgcca atgatctgac tcccgagcaa aaggtcgccg cggctgcgct cccggcgccg    840
gcggctgcag ccatcgtggc gggtccaaag cagaactgcg agcccgacct catgccctac    900
gcccgcccct ttgcagtagg caaaaggacc tgctccggca tcgtcacccc c             951
```

<210> SEQ ID NO 8
<211> LENGTH: 1023
<212> TYPE: DNA
<213> ORGANISM: Candida antarctica

<400> SEQUENCE: 8

```
atgaatatat tttacatatt tttgtttttg ctgtcattcg ttcaaggtac cgccactcct     60
ttggtgaagc gtctgccttc cggttcggac cctgcctttt cgcagcccaa gtcggtgctc    120
gatgcgggtc tgacctgcca gggtgcttcg ccatcctcgg tctccaaacc catccttctc    180
gtccccggaa ccggcaccac aggtccacag tcgttcgact cgaactggat ccccctctct    240
gcgcagctgg gttacacacc ctgctggatc tcacccccgc cgttcatgct caacgacacc    300
caggtcaaca cggagtacat ggtcaacgcc atcaccacgc tctacgctgg ttcgggcaac    360
aacaagcttc ccgtgctcac ctggtcccag ggtggtctgg ttgcacagtg gggtctgacc    420
ttcttcccca gtatcaggtc caaggtcgat cgacttatgg cctttgcgcc cgactacaag    480
ggcaccgtcc tcgccggccc tctcgatgca ctcgcggtta gtgcaccctc cgtatggcag    540
caaaccaccg gttcggcact cactaccgca ctccgaaacg caggtggtct gacccagatc    600
gtgcccacca ccaacctcta ctcggcgacc gacgagatcg ttcagcctca ggtgtccaac    660
tcgccactcg actcatccta ccttcttcaac ggaaagaacg tccaggcaca ggctgtgtgt    720
gggccgcagt tcgtcatcga ccatgcaggc tcgctcacct cgcagttctc ctacgtcgtc    780
ggtcgatccg ccctgcgctc caccacgggc caggctcgta gtgcagacta tggcattacg    840
gactgcaacc ctcttcccgc caatgatctg actcccgagc aaaaggtcgc cgcggctgcg    900
ctcctggcgc cggcggctgc agccatcgtg gcgggtccaa agcagaactg cgagcccgac    960
ctcatgccct acgcccgccc cttttgcagta ggcaaaagga cctgctccgg catcgtcacc   1020
ccc                                                                 1023
```

<210> SEQ ID NO 9
<211> LENGTH: 319
<212> TYPE: PRT
<213> ORGANISM: Candida antarctica

<400> SEQUENCE: 9

```
Leu Pro Ser Gly Ser Asp Pro Ala Phe Ser Gln Pro Lys Ser Val Leu
1               5                   10                  15
```

```
Asp Ala Gly Leu Thr Cys Gln Gly Ala Ser Pro Ser Ser Val Ser Lys
            20                  25                  30

Pro Ile Leu Leu Val Pro Gly Thr Gly Thr Thr Gly Pro Gln Ser Phe
            35                  40                  45

Asp Ser Asn Trp Ile Pro Leu Ser Ala Gln Leu Gly Tyr Thr Pro Cys
 50                  55                  60

Trp Ile Ser Pro Pro Pro Phe Met Leu Asn Asp Thr Gln Val Asn Thr
 65                  70                  75                  80

Glu Tyr Met Val Asn Ala Ile Thr Thr Leu Tyr Ala Gly Ser Gly Asn
                85                  90                  95

Asn Lys Leu Pro Val Leu Thr Trp Ser Gln Gly Gly Leu Val Ala Gln
            100                 105                 110

Trp Gly Leu Thr Phe Phe Pro Ser Ile Arg Ser Lys Val Asp Arg Leu
            115                 120                 125

Met Ala Phe Ala Pro Asp Tyr Lys Gly Thr Val Leu Ala Gly Pro Leu
130                 135                 140

Asp Ala Leu Ala Val Ser Ala Pro Ser Val Trp Gln Gln Thr Thr Gly
145                 150                 155                 160

Ser Ala Leu Thr Thr Ala Leu Arg Asn Ala Gly Gly Leu Thr Gln Ile
                165                 170                 175

Val Pro Thr Thr Asn Leu Tyr Ser Ala Thr Asp Glu Ile Val Gln Pro
            180                 185                 190

Gln Val Ser Asn Ser Pro Leu Asp Ser Ser Tyr Leu Phe Asn Gly Lys
            195                 200                 205

Asn Val Gln Ala Gln Ala Val Cys Gly Pro Leu Phe Val Ile Asp His
            210                 215                 220

Ala Gly Ser Leu Thr Ser Gln Phe Ser Tyr Val Val Gly Arg Ser Ala
225                 230                 235                 240

Leu Arg Ser Thr Thr Gly Gln Ala Arg Ser Ala Asp Tyr Gly Ile Thr
                245                 250                 255

Asp Cys Asn Pro Leu Pro Ala Asn Asp Leu Thr Pro Glu Gln Lys Val
            260                 265                 270

Ala Ala Ala Ala Leu Pro Ala Pro Ala Ala Ala Ile Val Ala Gly
            275                 280                 285

Pro Lys Gln Asn Cys Glu Pro Asp Leu Met Pro Tyr Ala Arg Pro Phe
            290                 295                 300

Ala Val Gly Lys Arg Thr Cys Ser Gly Ile Val Thr Pro Gly Ser
305                 310                 315

<210> SEQ ID NO 10
<211> LENGTH: 319
<212> TYPE: PRT
<213> ORGANISM: Candida antarctica

<400> SEQUENCE: 10

Leu Pro Ser Gly Ser Asp Pro Ala Phe Ser Gln Pro Lys Ser Val Leu
1                5                  10                  15

Asp Ala Gly Leu Thr Cys Gln Gly Ala Ser Pro Ser Ser Val Ser Lys
            20                  25                  30

Pro Ile Leu Leu Val Pro Gly Thr Gly Thr Thr Gly Pro Gln Ser Phe
            35                  40                  45

Asp Ser Asn Trp Ile Pro Leu Ser Ala Gln Leu Gly Tyr Thr Pro Cys
 50                  55                  60

Trp Ile Ser Pro Pro Pro Phe Met Leu Asn Asp Thr Gln Val Asn Thr
```

```
                65                  70                  75                  80
Glu Tyr Met Val Asn Ala Ile Thr Thr Leu Tyr Ala Gly Ser Gly Asn
                    85                  90                  95

Asn Lys Leu Pro Val Leu Thr Trp Ser Gln Gly Gly Leu Val Ala Gln
                100                 105                 110

Trp Gly Leu Thr Phe Phe Pro Ser Ile Arg Ser Lys Val Asp Arg Leu
                115                 120                 125

Met Ala Phe Ala Pro Asp Tyr Lys Gly Thr Val Leu Ala Gly Pro Leu
            130                 135                 140

Asp Ala Leu Ala Val Ser Ala Pro Ser Val Trp Gln Gln Thr Thr Gly
145                 150                 155                 160

Ser Ala Leu Thr Thr Ala Leu Arg Asn Ala Gly Gly Leu Thr Gln Ile
                165                 170                 175

Val Pro Thr Thr Asn Leu Tyr Ser Ala Thr Asp Glu Ile Val Gln Pro
                180                 185                 190

Gln Val Ser Asn Ser Pro Leu Asp Ser Ser Tyr Leu Phe Asn Gly Lys
                195                 200                 205

Asn Val Gln Ala Gln Ala Val Cys Gly Pro Gln Phe Val Ile Asp His
            210                 215                 220

Ala Gly Ser Leu Thr Ser Gln Phe Ser Tyr Val Val Gly Arg Ser Ala
225                 230                 235                 240

Leu Arg Ser Thr Thr Gly Gln Ala Arg Ser Ala Asp Tyr Gly Ile Thr
                245                 250                 255

Asp Cys Asn Pro Leu Pro Ala Asn Asp Leu Thr Pro Glu Gln Lys Val
                260                 265                 270

Ala Ala Ala Ala Leu Pro Ala Pro Ala Ala Ala Ile Val Ala Gly
            275                 280                 285

Pro Lys Gln Asn Cys Glu Pro Asp Leu Met Pro Tyr Ala Arg Pro Phe
            290                 295                 300

Ala Val Gly Lys Arg Thr Cys Ser Gly Ile Val Thr Pro Gly Ser
305                 310                 315

<210> SEQ ID NO 11
<211> LENGTH: 317
<212> TYPE: PRT
<213> ORGANISM: Candida antarctica

<400> SEQUENCE: 11

Leu Pro Ser Gly Ser Asp Pro Ala Phe Ser Gln Pro Lys Ser Val Leu
1               5                   10                  15

Asp Ala Gly Leu Thr Cys Gln Gly Ala Ser Pro Ser Ser Val Ser Lys
                20                  25                  30

Pro Ile Leu Leu Val Pro Gly Thr Gly Thr Thr Gly Pro Gln Ser Phe
                35                  40                  45

Asp Ser Asn Trp Ile Pro Leu Ser Ala Gln Leu Gly Tyr Thr Pro Cys
            50                  55                  60

Trp Ile Ser Pro Pro Pro Phe Met Leu Asn Asp Thr Gln Val Asn Thr
65                  70                  75                  80

Glu Tyr Met Val Asn Ala Ile Thr Thr Leu Tyr Ala Gly Ser Gly Asn
                    85                  90                  95

Asn Lys Leu Pro Val Leu Thr Trp Ser Gln Gly Gly Leu Val Ala Gln
                100                 105                 110

Trp Gly Leu Thr Phe Phe Pro Ser Ile Arg Ser Lys Val Asp Arg Leu
                115                 120                 125
```

```
Met Ala Phe Ala Pro Asp Tyr Lys Gly Thr Val Leu Ala Gly Pro Leu
            130                 135                 140

Asp Ala Leu Ala Val Ser Ala Pro Ser Val Trp Gln Gln Thr Thr Gly
145                 150                 155                 160

Ser Ala Leu Thr Thr Ala Leu Arg Asn Ala Gly Gly Leu Thr Gln Ile
                165                 170                 175

Val Pro Thr Thr Asn Leu Tyr Ser Ala Thr Asp Glu Ile Val Gln Pro
                180                 185                 190

Gln Val Ser Asn Ser Pro Leu Asp Ser Ser Tyr Leu Phe Asn Gly Lys
                195                 200                 205

Asn Val Gln Ala Gln Ala Val Cys Gly Pro Gln Phe Val Ile Asp His
            210                 215                 220

Ala Gly Ser Leu Thr Ser Gln Phe Ser Tyr Val Val Gly Arg Ser Ala
225                 230                 235                 240

Leu Arg Ser Thr Thr Gly Gln Ala Arg Ser Ala Asp Tyr Gly Ile Thr
                245                 250                 255

Asp Cys Asn Pro Leu Pro Ala Asn Asp Leu Thr Pro Glu Gln Lys Val
                260                 265                 270

Ala Ala Ala Ala Leu Leu Ala Pro Ala Ala Ala Ile Val Ala Gly
                275                 280                 285

Pro Lys Gln Asn Cys Glu Pro Asp Leu Met Pro Tyr Ala Arg Pro Phe
            290                 295                 300

Ala Val Gly Lys Arg Thr Cys Ser Gly Ile Val Thr Pro
305                 310                 315
```

<210> SEQ ID NO 12
<211> LENGTH: 26
<212> TYPE: DNA
<213> ORGANISM: Artificial Sequence
<220> FEATURE:
<223> OTHER INFORMATION: CALB primer 4

<400> SEQUENCE: 12
ctcatatgct accttccggt tcggac                                    26

<210> SEQ ID NO 13
<211> LENGTH: 21
<212> TYPE: PRT
<213> ORGANISM: Artificial Sequence
<220> FEATURE:
<223> OTHER INFORMATION: a-amylase secretion signal

<400> SEQUENCE: 13

```
Met Met Val Ala Trp Trp Ser Leu Phe Leu Tyr Gly Leu Gln Val Ala
1               5                   10                  15

Ala Pro Ala Leu Ala
            20
```

<210> SEQ ID NO 14
<211> LENGTH: 317
<212> TYPE: PRT
<213> ORGANISM: Candida antarctica

<400> SEQUENCE: 14

```
Leu Pro Ser Gly Ser Asp Pro Ala Phe Ser Gln Pro Lys Ser Val Leu
1               5                   10                  15

Asp Ala Gly Leu Thr Cys Gln Gly Ala Ser Pro Ser Ser Val Ser Lys
                20                  25                  30

Pro Ile Leu Leu Val Pro Gly Thr Gly Thr Thr Gly Pro Gln Ser Phe
```

```
                 35                  40                  45

Asp Ser Asn Trp Ile Pro Leu Ser Ala Gln Leu Gly Tyr Thr Pro Cys
 50                  55                  60

Trp Ile Ser Pro Pro Phe Met Leu Asn Asp Thr Gln Val Asn Thr
 65                  70                  75                  80

Glu Tyr Met Val Asn Ala Ile Thr Thr Leu Tyr Ala Gly Ser Gly Asn
                     85                  90                  95

Asn Lys Leu Pro Val Leu Thr Trp Ser Gln Gly Leu Val Ala Gln
                100                 105                 110

Trp Gly Leu Thr Phe Phe Pro Ser Ile Arg Ser Lys Val Asp Arg Leu
                115                 120                 125

Met Ala Phe Ala Pro Asp Tyr Lys Gly Thr Val Leu Ala Gly Pro Leu
130                 135                 140

Asp Ala Leu Ala Val Ser Ala Pro Ser Val Trp Gln Gln Thr Thr Gly
145                 150                 155                 160

Ser Ala Leu Thr Thr Ala Leu Arg Asn Ala Gly Gly Leu Thr Gln Ile
                165                 170                 175

Val Pro Thr Thr Asn Leu Tyr Ser Ala Thr Asp Glu Ile Val Gln Pro
                180                 185                 190

Gln Val Ser Asn Ser Pro Leu Asp Ser Ser Tyr Leu Phe Asn Gly Lys
                195                 200                 205

Asn Val Gln Ala Gln Ala Val Cys Gly Pro Leu Phe Val Ile Asp His
                210                 215                 220

Ala Gly Ser Leu Thr Ser Gln Phe Ser Tyr Val Val Gly Arg Ser Ala
225                 230                 235                 240

Leu Arg Ser Thr Thr Gly Gln Ala Arg Ser Ala Asp Tyr Gly Ile Thr
                245                 250                 255

Asp Cys Asn Pro Leu Pro Ala Asn Asp Leu Thr Pro Glu Gln Lys Val
                260                 265                 270

Ala Ala Ala Ala Leu Leu Ala Pro Ala Ala Ala Ile Val Ala Gly
                275                 280                 285

Pro Lys Gln Asn Cys Glu Pro Asp Leu Met Pro Tyr Ala Arg Pro Phe
                290                 295                 300

Ala Val Gly Lys Arg Thr Cys Ser Gly Ile Val Thr Pro
305                 310                 315

<210> SEQ ID NO 15
<211> LENGTH: 28
<212> TYPE: DNA
<213> ORGANISM: Artificial Sequence
<220> FEATURE:
<223> OTHER INFORMATION: LQ53 primer

<400> SEQUENCE: 15
gctgtgtgtg ggccgcagtt cgtcatcg                                      28

<210> SEQ ID NO 16
<211> LENGTH: 30
<212> TYPE: DNA
<213> ORGANISM: Artificial Sequence
<220> FEATURE:
<223> OTHER INFORMATION: LQ35 primer

<400> SEQUENCE: 16
gcatggtcga tgacgaactg cggcccacac                                    30

<210> SEQ ID NO 17
```

<211> LENGTH: 30
<212> TYPE: DNA
<213> ORGANISM: Artificial Sequence
<220> FEATURE:
<223> OTHER INFORMATION: LP53 primer

<400> SEQUENCE: 17
gtcgccgcgg ctgcgctccc ggcgccggcg                                    30

<210> SEQ ID NO 18
<211> LENGTH: 29
<212> TYPE: DNA
<213> ORGANISM: Artificial Sequence
<220> FEATURE:
<223> OTHER INFORMATION: LP35 primer

<400> SEQUENCE: 18
ctgcagccgc cggcgccggg agcgcagcc                                     29

<210> SEQ ID NO 19
<211> LENGTH: 343
<212> TYPE: PRT
<213> ORGANISM: Candida antarctica

<400> SEQUENCE: 19

Met Asn Ile Phe Tyr Ile Phe Leu Phe Leu Leu Ser Phe Val Gln Gly
1               5                   10                  15

Thr Ala Thr Pro Leu Val Lys Arg Leu Pro Ser Gly Ser Asp Pro Ala
            20                  25                  30

Phe Ser Gln Pro Lys Ser Val Leu Asp Ala Gly Leu Thr Cys Gln Gly
        35                  40                  45

Ala Ser Pro Ser Ser Val Ser Lys Pro Ile Leu Leu Val Pro Gly Thr
    50                  55                  60

Gly Thr Thr Gly Pro Gln Ser Phe Asp Ser Asn Trp Ile Pro Leu Ser
65                  70                  75                  80

Ala Gln Leu Gly Tyr Thr Pro Cys Trp Ile Ser Pro Pro Pro Phe Met
                85                  90                  95

Leu Asn Asp Thr Gln Val Asn Thr Glu Tyr Met Val Asn Ala Ile Thr
            100                 105                 110

Thr Leu Tyr Ala Gly Ser Gly Asn Asn Lys Leu Pro Val Leu Thr Trp
        115                 120                 125

Ser Gln Gly Gly Leu Val Ala Gln Trp Gly Leu Thr Phe Phe Pro Ser
    130                 135                 140

Ile Arg Ser Lys Val Asp Arg Leu Met Ala Phe Ala Pro Asp Tyr Lys
145                 150                 155                 160

Gly Thr Val Leu Ala Gly Pro Leu Asp Ala Leu Ala Val Ser Ala Pro
                165                 170                 175

Ser Val Trp Gln Gln Thr Thr Gly Ser Ala Leu Thr Thr Ala Leu Arg
            180                 185                 190

Asn Ala Gly Gly Leu Thr Gln Ile Val Pro Thr Thr Asn Leu Tyr Ser
        195                 200                 205

Ala Thr Asp Glu Ile Val Gln Pro Gln Val Ser Asn Ser Pro Leu Asp
    210                 215                 220

Ser Ser Tyr Leu Phe Asn Gly Lys Asn Val Gln Ala Gln Ala Val Cys
225                 230                 235                 240

Gly Pro Leu Phe Val Ile Asp His Ala Gly Ser Leu Thr Ser Gln Phe
                245                 250                 255

Ser Tyr Val Val Gly Arg Ser Ala Leu Arg Ser Thr Thr Gly Gln Ala

```
                    260                 265                 270
Arg Ser Ala Asp Tyr Gly Ile Thr Asp Cys Asn Pro Leu Pro Ala Asn
        275                 280                 285

Asp Leu Thr Pro Glu Gln Lys Val Ala Ala Ala Leu Leu Ala Pro
        290             295             300

Ala Ala Ala Ala Ile Val Ala Gly Pro Lys Gln Asn Cys Glu Pro Asp
305             310             315                 320

Leu Met Pro Tyr Ala Arg Pro Phe Ala Val Gly Lys Arg Thr Cys Ser
            325             330             335

Gly Ile Val Thr Pro Gly Ser
            340
```